United States Patent
Berry et al.

(10) Patent No.: US 10,765,622 B2
(45) Date of Patent: Sep. 8, 2020

(54) PROCESS FOR THE PRODUCTION OF A COMPOSITION FOR PROTECTING SKIN FROM DRYING AND/OR UV DAMAGE AND/OR INFLAMMATION

(71) Applicant: Conopco, Inc., Englewood Cliffs, NJ (US)

(72) Inventors: Mark John Berry, Higham Ferrers (GB); Ravine Anthony Gungabissoon, Marston Moretaine (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 128 days.

(21) Appl. No.: 16/092,869

(22) PCT Filed: Mar. 30, 2017

(86) PCT No.: PCT/EP2017/057511
§ 371 (c)(1),
(2) Date: Oct. 11, 2018

(87) PCT Pub. No.: WO2017/178238
PCT Pub. Date: Oct. 19, 2017

(65) Prior Publication Data
US 2019/0151228 A1 May 23, 2019

(30) Foreign Application Priority Data
Apr. 14, 2016 (EP) .................... 16165271

(51) Int. Cl.
| C12N 5/04 | (2006.01) |
| A61K 8/9789 | (2017.01) |
| A61Q 17/04 | (2006.01) |
| A61Q 19/00 | (2006.01) |
| A61K 8/97 | (2017.01) |

(52) U.S. Cl.
CPC .............. *A61K 8/9789* (2017.08); *A61K 8/97* (2013.01); *A61Q 17/04* (2013.01); *A61Q 19/007* (2013.01); *C12N 5/04* (2013.01)

(58) Field of Classification Search
CPC ........................................................ C12N 5/04
See application file for complete search history.

(56) References Cited

U.S. PATENT DOCUMENTS

| 2010/0136636 A1 | 6/2010 | Takemoto |
| 2014/0186315 A1 | 7/2014 | Kang et al. |

FOREIGN PATENT DOCUMENTS

| EP | 20110031801 | 3/2011 |
| WO | WO2013060710 | 5/2013 |

OTHER PUBLICATIONS

IPRP2 in PCTEP2017057511; Jul. 27, 2018.
Anonymous; Green tea helps protect skin from sun damage; Internet article from nyrnaturalnews.com; Feb. 14, 2014; XP002761638; pp. 1-4 Website: www..nyrnaturalnews.com/herbal-remedies/2013/02/green-tea-helps-protect-skin-from-sun-damage/.
Search Report and Written Opinioin in EP16165271; dated Oct. 11, 2016.
Search Report and Written Opinion in PCTEP2017057511 ; May 24, 2017.

*Primary Examiner* — Rosanne Kosson
(74) *Attorney, Agent, or Firm* — Stephanie Huang

(57) ABSTRACT

A process for the production of a *Camellia sinensis* dedifferentiated stem cell extract, the process comprising the steps of: (a) Preparing a cell culture comprising *Camellia sinensis* dedifferentiated stem cells; (b) Performing an extraction on the cell culture using ethanol and/or methanol as an extraction solvent, to produce the *Camellia sinensis* dedifferentiated stem cell extract.

8 Claims, No Drawings

PROCESS FOR THE PRODUCTION OF A COMPOSITION FOR PROTECTING SKIN FROM DRYING AND/OR UV DAMAGE AND/OR INFLAMMATION

FIELD OF THE INVENTION

The invention relates to a process for the production of a *Camellia sinensis* dedifferentiated stem cell culture extract, to a composition comprising such an extract and to the use of such an extract.

BACKGROUND OF THE INVENTION

It is commonly desirable for people to prefer healthy skin. However, environmental factors cause damage to skin/hair and make skin/hair less healthy and less resilient to stresses such as UV and drying.

In general consumers find it convenient to apply topical compositions to their skin and even consume particular products, in order to provide improved appearance or protection of the skin.

Additionally, consumers have a general preference for natural components and a general reluctance to use more synthetic compositions, particularly if they are to consume the composition.

US2014/0186315 discloses a cosmetic composition which contains a green tea stem cell extract. The composition is stated to be an anti-aging composition. The green tea stem cell is made by culturing a totipotent callus in a cell culture. The active ingredient is said to be extracted from the cell culture. However no details regarding the extraction process are provided.

Further improvements in this area would therefore be desirable.

SUMMARY OF THE INVENTION

We have found that specific cell culture extracts of *Camellia sinensis* can be used to improve skin health. More particularly we have found that dedifferentiated stem cell culture extracts of *Camellia sinensis* deliver resistance to environmental damage of skin cells such.

Therefore, in a first aspect the invention relates to a process for the production of a *Camellia sinensis* dedifferentiated stem cell extract, the process comprising the steps of:
  (a) Preparing a cell culture comprising dedifferentiated *Camellia sinensis* stem cells;
  (b) Performing an extraction on the cell culture using ethanol and/or methanol as an extraction solvent, to produce the *Camellia sinensis* dedifferentiated cell culture extract.

Such an extract of dedifferentiated stem cells has been found to provide surprising protection of skin cells against cell damage caused by drying and ultraviolet light as well as providing an anti-inflammatory effect.

It is believed that the ethanol and methanol provide a higher concentration of certain actives within the stem cell extract, such as flavanones, polyphenols and terpenoids. It has been found that other solvents produce a stem cell extract that is noticeably inferior.

Thus, in a second aspect, the invention relates to a composition, comprising a *Camellia sinensis* dedifferentiated stem cell extract obtainable by the process as described herein.

It has furthermore been found that such dedifferentiated stem cell extracts have a strong and clear protective effect on skin cells when exposed to drying or UV radiation and also reduce inflammation.

Thus, in a third aspect, the invention relates to the use of a *Camellia sinensis* dedifferentiated stem cell extract for protecting skin from drying and/or UV damage and/or inflammation.

DETAILED DESCRIPTION OF THE INVENTION

Tea refers to one or more plants belonging to the family of *Camellia sinensis* var. *sinensis* and/or *Camellia sinensis* var. *assamica*. Tea is the second most consumed beverage worldwide. It is rich source of monomeric and polymeric forms of the flavonoids and can account up to 10-30% flavonoids by weight.

In this invention extracts are prepared from dedifferentiated tea stem cells. Dedifferentiated tea stem cells can be conveniently prepared from callus which is a response to wounding.

Plant callus is a mass of unorganized parenchyma cells derived from plant tissue (explants). In plant biology, callus cells are those cells that cover a plant wound. Callus formation is induced from plant tissues after surface sterilization and plating onto in vitro tissue culture medium. Plant growth regulators, such as auxins, cytokinins, and gibberellins, are supplemented into the medium to initiate callus formation or somatic embryogenesis.

In general, the plant callus cells are obtained by growing the cells in culture. Plant callus material can be obtained and cut from an explant and transferred to a culture medium. Once in the culture medium the cells can be grown as desired until a sufficient quantity is obtained. Callus can be grown on solid growth media such as agar and then transferred to liquid growth media to bulk up the production and to harvest active components by extraction.

The cell culture process can be carried out in a way known in the art.

Preferably the cell culture media comprises the Hormones 2,4-Dichlorophenoxyacetic acid (2,4-D), Naphthaleneacetic acid (NAA) and 6-Benzylamino purine (BAP).

Preferably the cell culture media has a pH of from 5.6 to 6.0.

Preferably the composition of the invention comprises the stem cell extract at a concentration of greater than 0.01 wt %.

The composition of the invention comprises a cosmetically acceptable base when it is a topical composition. The cosmetically acceptable base as per the present invention is a cream, lotion, gel or emulsion. The cosmetically acceptable base preferably comprises a fatty acid or a silicone compound. When the cosmetically acceptable base comprises fatty acid it is preferably present in 1 to 25% by weight of the composition. When the cosmetically acceptable bases are such as to have a product in a cream, lotion, or emulsion format, it generally comprises fatty acid. Of these formats, a more preferred format is a cream or lotion, further more preferably a cream. Vanishing cream base is one which comprises 3 to 25%, more preferably 5 to 20% fatty acid, which is a preferred format of the composition of the invention. In this, the base preferably comprises 0.1 to 10%, more preferably 0.1 to 3% soap. $C_{12}$ to $C_{20}$ fatty acids are especially preferred in vanishing cream bases, further more preferred being $C_{14}$ to $C_{18}$ fatty acids. In creams, the fatty acid is preferably substantially a mixture of stearic acid and palmitic acid. Soaps in the vanishing cream base include alkali metal salt of fatty acids, like sodium or potassium salts. The soap is preferably the potassium salt of the fatty acid mixture. The fatty acid in vanishing cream base is often prepared using hystric acid which is substantially (generally about 90 to 95%) a mixture of stearic acid and palmitic acid (usually 55% stearic acid and 45% palmitic acid). Thus, inclusion of hystric acid and its soap to prepare the vanishing cream base is within the scope of the present invention. It is particularly preferred that the composition comprises at least 6%, preferably at least 10%, more preferably at least 12% fatty acid. The cosmetically acceptable base is usually from 10 to 99.9%, preferably from 50 to 99% by weight of the composition. Another preferred base is a lotion. Lotions generally comprise 1 to 20% fatty acid. The cosmetically acceptable base preferably includes water. Water is preferably included in 35 to 90%, more preferably 50 to 85%, further more preferably 50 to 80% by weight of the composition.

An especially suitable cosmetically acceptable base is one which comprises a water-in-oil emulsion comprising silicone oils as the continuous phase. The water in oil emulsions preferably comprise a crosslinked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 50% silicone elastomer by weight of the composition.

Useful sun-protective agents e.g. inorganic sun-blocks may be preferably used in the present invention. These include, for example, zinc oxide, iron oxide, silica, such as fumed silica, or titanium dioxide. The total amount of sun block that is preferably incorporated in the composition according to the invention is from 0.1 to 5% by weight of the composition.

The topical composition of the invention may additionally comprise a skin lightening agent. The skin lightening agent is preferably chosen from a vitamin B3 compound or its derivative e.g. niacin, nicotinic acid, niacinamide or other well-known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The topical composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The topical compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

When the composition is an oral composition, the composition may take the form of a food or beverage product. In general such an oral product may take any suitable form of consumable product such as a drink, a bar, a meal, or a supplement.

EXAMPLES

Tea Callus Cell Culture
  Young leaves from Sri Lanka clone 2 (*Camellia sinensis assimica*) were sterilised as follows:
    Soak in water with a few drops of tween 20 for 30 mins.
    Wash under running water for 15 mins.
    Surface sterilise in hydrogen peroxide for 2 mins.
    Wash under running water
    Surface sterilise in 70% ethanol for 2 mins.
    Wash under running water
    Transfer to flow hood and surface sterilise with 10% domestic bleach for 30 mins.
    Wash with distilled water (in the hood)
    Cut leaves into squares (explants) and transfer to media in petri dishes
  Solid Media Composition:
    MS medium (salts and vits)
    30 g/L sucrose
    0.8% agar
    pH adjust to 5.8 with 0.2M KOH
    Hormones 0.25 mg $L^{-1}$ 2,4-Dichlorophenoxyacetic acid (2,4-D), 0.25 mg $L^{-1}$ Naphthaleneacetic acid (NAA) and 1 mg $L^{-1}$ 6-Benzylamino purine (BAP).
  The medium was sterilised by autoclaving at 121° C. for 30 mins. After autoclaving the medium was allowed to cool to 60° C. before it was poured into 9 cm petri dishes (approximately 10 ml per plate). The agar was set by cooling to 4° C.
  5 to 10 tea leaf explants were grown in each petri dish of solid medium at 25° C.±2 on a cycle of 16 h light and 8 h dark in a plant growth cabinet
  Agglomerations of callus developing on the wounded areas of the explant were carefully removed after sufficient growth and subcultured on a fresh petri dish of solid medium.
  Agglomeration of callus cells were subcultured onto fresh solid media every 4 weeks. Subculturing is simply transferring the callus culture to fresh media. This is necessary because the solid agar gel medium dries out over time (approx. 3-4 weeks) and the growing callus needs to be kept hydrated.
  After 12 weeks the callus were of sufficient size (approx. 1-2 cm in diameter) for further experimentation.
  At this stage the callus was fully freeze dried for 48 hours and stored at −20° C. until required
Preparation of the Tea Callus Cell Extracts
  A 20% suspension of freeze dried callus material was prepared in 96% Ethanol 0.1 g of freeze dried material was mixed with 0.9 g of 96% Ethanol. Note: this is not a 10/90 wt % callus:ethanol solution as the majority of callus material is insoluble and remains in suspension. By weighing the dry mass of insoluble material after solvent extraction the approximate final concentration of soluble extract was calculated to be 10 mg/ml. Therefore, in the cell survival assays 1%=0.1 mg/ml soluble extract.

The suspension was vortexed vigorously for 1 min and then placed in a sonication bath and sonicated for 30 mins between 0-4° C.

The suspension was centrifuged at 13,000 rpm for 10 mins at 4° C. and the supernatant retained (stem cell extract stock solution)

The stem cell extract stock solution was stored at −20° C. until use

Skin Cell Drying Protection Assay

Human Adult Dermal Fibroblasts (Cat no. C-013-5C, Life Technologies) were cultured to approximately 90% confluency in 24 well plates containing 0.5 ml Medium 106 (Cat no. M-106-500, Life Technologies) supplemented with Low Serum Growth Supplement (Cat no. S-003-10, Life Technologies) at 37° C., 5% $CO_2$ Stem Cell Extract was added to the medium to final concentrations of either 0.1%, 0.5% or 1%.

An experimental control containing 1% Ethanol (carrier only) was also prepared

The cells were then grown for a further 24 hours

The cells were dried by completely aspirating the medium from the wells and leaving them for 10 mins in a laminar flow cell culture hood at room temperature.

Non-dried controls were included for each condition 0.5 ml of fresh medium was then added to each well and the cells incubated at 37° C., 5% $CO_2$ After 1 hour 50 µl of AlamarBlue Cell Viability Reagent (Molecular Probes, Cat no. DAL1025) was added to each well After a further 4 hours of incubation at 37° C., 5% $CO_2$, 200 µl of medium was removed from each well and placed into 96 well plate. The fluorescent intensity of the samples were read at excitation 550 nm/emission 612 nm. AlamarBlue works as a cell viability indicator through the conversion of a non-fluorescent dye (resazurin) to a highly fluorescent dye (resorufin) via reduction reactions in metabolically active cells.

Skin Cell Ultraviolet Protection Assay

Human Adult Dermal Fibroblasts (Cat no. C-013-5C, Life Technologies) were cultured to approximately 90% confluency in 6 cm petri dishes containing 1 ml DMEM (Life Technologies, Cat No. 21063-029) supplemented with 1 mM pyruvate, 2 mM Glutamine and 10% Foetal Calf Serum at 37° C., 5% $CO_2$ Stem Cell Extract was added to the medium to final concentrations of either 0.1%, 0.5% or 1%.

An experimental control containing 1% Ethanol (carrier only) was also prepared

The cells were then grown for a further 24 hours

Lids were removed from the petri dishes and the cells irradiated in a Uvacube 400 ultraviolet chamber (Honle UV technology) for 30 mins Old media was removed and fresh medium of the same type added was added The cells were incubated at 37° C., 5% $CO_2$ for 24 hours.

100 µl of AlamarBlue Cell Viability Reagent (Molecular Probes, Cat no. DAL1025) was then added to each well and incubation continued for a further 24 hours.

200 µl of medium was removed from each well and placed into a 96 well plate. The fluorescent intensity of the samples were then read at excitation 550 nm/emission 612 nm. AlamarBlue works as a cell viability indicator through the conversion of a non-fluorescent dye (resazurin) to a highly fluorescent dye (resorufin) via reduction reactions in metabolically active cells.

Anti-Inflammatory Assay

Human adult dermal fibroblasts (Cat no. C-013-5C, Life Technologies) were grown to a concentration of 60,000 cells per well in 12 well plates containing 1 ml DMEM GlutaMAX (Gibco, Cat No. 10566016) supplemented with 1% Foetal Calf Serum per well at 37° C., 5% $CO_2$ Tea Callus Extract was added to each well containing 1 ml of medium at a final concentration of 1%. At the same time, Phorbol 12-myristate 13-acetate (PMA, Cat no. P8139 Sigma) was also added to each well at a final concentration of 100 nm.

An experimental control containing 1% Ethanol (carrier only) and 100 nm PMA was also prepared The cells were incubated at 37° C., 5% $CO_2$ for a further 24 hrs The cell culture medium was then removed and centrifuged at 16,000 RPM for 1 min. The supernatant was collected and stored at −20° C. until needed.

The cells were washed 3 times with PBS and then lysed by the addition of 1 ml per well RIPA Lysis and Extraction Buffer (Cat no. 8990, Thermo Scientific) for 30 mins on ice.

The cell lysates were collected and centrifuged at 16,000 RPM for 1 min. The lysate supernatants were collected and assayed for total protein content using a BCA Protein Assay Kit (Cat no. 23225, Thermo Scientific)

IL-6 content in the cell media supernatants was measured using the Quantikine ELISA Human IL-6 Immunoassay Kit (Cat no. D6050, R&D Systems). The total protein content for each well was used to normalise the IL-6 concentrations measured. This allowed the IL-6 levels in each sample to be compared directly.

Skin Cell Drying Assay (Tea Extract)

TABLE 1

AlamarBlue fluorescence measurements of media from human dermal fibroblasts read at ex. 550 nm/em. 612 nm. Three replicates (Sample 1-3) were carried out for each condition. The fluorescent intensity of the medium and AlamarBlue alone (Background fluorescence) was subtracted from the average values.

|  | Sample 1 | Sample 2 | Sample 3 | Average | Average − Background | Standard Deviation |
| --- | --- | --- | --- | --- | --- | --- |
| Ethanol 1% | 58628 | 56283 | 57194 | 57368 | 43116 | 1182 |
| Ethanol 1% (Dried) | 15997 | 14981 | 15763 | 15580 | 1328 | 532 |
| Tea Callus Extract 1% | 49562 | 48734 | 49178 | 49158 | 34906 | 414 |
| Tea Callus Extract 1% (Dried) | 49698 | 46815 | 47935 | 48149 | 33897 | 1453 |
| Tea Callus Extract 0.5% | 51018 | 53845 | 51933 | 52265 | 38013 | 1443 |
| Tea Callus Extract 0.5% (Dried) | 52006 | 51307 | 50602 | 51305 | 37053 | 702 |
| Tea Callus Extract 0.1% | 53646 | 54813 | 52708 | 53722 | 39470 | 1055 |
| Tea Extract 0.1% (Dried) | 51737 | 52091 | 51445 | 51758 | 37506 | 323 |
| Tea Callus Extract 0.01% | 54996 | 55830 | 57119 | 55982 | 41730 | 1070 |

TABLE 1-continued

AlamarBlue fluorescence measurements of media from human dermal fibroblasts
read at ex. 550 nm/em. 612 nm. Three replicates (Sample 1-3) were carried out
for each condition. The fluorescent intensity of the medium and AlamarBlue
alone (Background fluorescence) was subtracted from the average values.

|  | Sample 1 | Sample 2 | Sample 3 | Average | Average − Background | Standard Deviation |
|---|---|---|---|---|---|---|
| Tea Callus Extract 0.01% (Dried) | 29888 | 32796 | 32395 | 31693 | 17441 | 1576 |
| Tea Leaf Extract 1% | 55931 | 53284 | 55993 | 55069 | 40817 | 1546 |
| Tea Leaf Extract 1% (Dried) | 26835 | 24405 | 24183 | 25141 | 10889 | 1471 |

These results show that the number of viable cells post-drying in the tea stem cell extract treated samples is higher than that for cells treated with the carrier (Ethanol) alone. Furthermore it shows that levels above 0.01 wt % provide a very significant protective effect.

A comparative example is also shown where extract from a tea leaf without generating callus is generated. Whilst there is some protective effect from this, it is not as great as the protective effect provided by the Callus extract.

Skin Cell Drying Assay (Tea Extract) Using Different Extraction Solvents

A 20% suspension of ground, freeze dried callus material was prepared in the following solvents: Ethanol, Methanol, Chloroform, Ether, Acetone, Water The suspension was vortexed vigorously for 1 min and then placed in a sonication bath and sonicated for 30 mins at 4° C.

The suspension was centrifuged at 13,000 rpm for 10 mins at 4° C. and the supernatant retained The supernatants were vacuum dried to evaporate off solvent The residual solid extract was dissolved in 1 ml DMSO (vortexed vigorously for 1 min)

The extracts were then used in the skin cell drying assay at a concentration of 1% in the final media as described An experimental control containing 1% DMSO (carrier only) was also prepared

TABLE 2

AlamarBlue fluorescence measurements of media from human dermal fibroblasts
read at ex. 550 nm/em. 612 nm. Three replicates (Sample 1-3) were carried out
for each condition. The fluorescent intensity of the medium and AlamarBlue
alone (Background fluorescence) was subtracted from the average values.

|  | Sample 1 | Sample 2 | Sample 3 | Average | Average − Background | Standard Deviation |
|---|---|---|---|---|---|---|
| Ethanol | 29326 | 31414 | 28234 | 29658 | 25556 | 1616 |
| Methanol | 25170 | 28037 | 26653 | 26620 | 22518 | 1434 |
| Chloroform | 17636 | 16629 | 16577 | 16947 | 12845 | 597 |
| Ether | 12086 | 10611 | 11134 | 11277 | 7175 | 748 |
| Acetone | 14513 | 13648 | 13109 | 13757 | 9655 | 708 |
| Water | 8318 | 8502 | 9652 | 8824 | 4722 | 723 |
| 1% DMSO | 6473 | 7915 | 6600 | 6996 | 2894 | 798 |

It can be seen that the skin cells treated with the cell culture extracts obtained with the solvents ethanol and methanol provide significantly better results that those obtained with other solvents.

Skin Cell Ultraviolet Protection Assay (Tea Extract)

TABLE 3

AlamarBlue fluorescence measurements of media from human dermal fibroblasts
read at ex. 550 nm/em. 612 nm. Three replicates (Sample 1-3) were carried out
for each condition. The fluorescent intensity of the medium and AlamarBlue
alone (Background fluorescence) was subtracted from the average values.

|  | Sample 1 | Sample 2 | Sample 3 | Average | Average − Background | Standard Deviation |
|---|---|---|---|---|---|---|
| 1% Ethanol | 79483 | 82725 | 78281 | 80163 | 68116 | 2231 |
| 1% Ethanol UV | 45928 | 43754 | 40549 | 43410 | 31363 | 1760 |
| Tea 0.1% | 83024 | 84153 | 80945 | 82707 | 70660 | 1607 |
| Tea 0.1% UV | 48142 | 49513 | 47035 | 48230 | 36183 | 1239 |
| Tea 0.5% | 78582 | 84031 | 81842 | 81485 | 69438 | 1378 |
| Tea 0.5% UV | 55000 | 59546 | 56014 | 56853 | 44806 | 1845 |
| Tea 1% | 85676 | 83877 | 81033 | 83529 | 71482 | 1551 |
| Tea 1% UV | 58303 | 64814 | 61758 | 61625 | 49578 | 1804 |

These results show that the number of viable cells post-UV irradiation in the tea callus cell extract treated samples is higher than that for cells treated with the carrier (Ethanol) alone. The effect appears to be dose dependent.

Anti-Inflammatory Assay

TABLE 4

Shows the concentration of Interleukin-6 (pg IL-6/ug of total cell protein) produced by human adult dermal fibroblasts treated with the inflammatory pathway activator PMA and either 1% tea callus extract or 1% ethanol (control). Three replicates (Sample 1-3) were carried out for each treatment. The results show that the tea callus extract lowers the amount of IL-6 produced in the PMA-treated cells indicating anti-inflammatory activity.

|  | Sample 1 | Sample 2 | Sample 3 | Average | Standard Deviation |
|---|---|---|---|---|---|
| 1% Tea Callus Extract + PMA | 9.32 | 8.65 | 8.34 | 8.77 | 0.50 |
| 1% Ethanol + PMA | 11.16 | 10.78 | 10.74 | 10.89 | 0.23 |

Chemical Analysis of Common Gallated and Non-Gallated Catechins in the Tea Callus Extract Samples:
  Tea Leaf leaves harvested in June 2015
  Tea Callus (old) older batch of tea callus cultured at beginning of 2015.
  Tea Callus (new) newer batch of tea callus cultured towards the end of 2015/beginning of 2016.

A 10-μl aliquot was injected onto a BEH C18 column (100×2.1 mm, 1.7 μm, Waters) on a Waters Acquity UPLC with a Xevo Triple Quadrupole Mass spectrometer. The mobile phase consists of a methanol (0.1% v/v formic acid)/water (0.1% v/v formic acid) gradient (10:90 to 60:40 over 10 min; to 2:98 over 1 min; hold for 2 min; to 10:90 over 1 min; hold for 1 min) at a flow rate of 0.2 ml/min and a column temperature of 40° C. The data was presented in the Waters MassLynx 4.1 software. Amounts of each metabolite was established by monitoring specific transitions in MRM mode (Epicatechin/Catechin: 289>245, Epigallocatechin: 305>125, Epicatechin gallate: 441>169, Epigallocatechin gallate: 457>169, Methyl gallate: 183.1>124, Gallic acid: 169>125).

This shows that the tea leaf sample has significantly more gallates than the callus samples (e.g. ~100 times more in the case of EGCG).

TABLE 5

Measured levels of various tea components. This data is expressed in relative terms as area under the curve (AUC).

|  | Tea Leaf | Callus (A) | Callus (B) |
|---|---|---|---|
| Gallic acid | 19749 | 349 | 588 |
| Methyl gallic | 138289 | 684 | 1702 |
| EGCG | 697159 | 5798 | 7692 |
| Epicatechin | 62686 | 13078 | 68280 |
| ECG | 319658 | 4014 | 41479 |
| EGC | 106309 | 1187 | 3950 |
| Catechin | 278696 | 154930 | 172515 |

The invention claimed is:

1. A process for the production of a *Camellia sinensis* dedifferentiated stem cell extract, the process comprising the steps of:
    (a) preparing a cell culture comprising *Camellia sinensis* dedifferentiated stem cells; and
    (b) performing a one-step extraction of the cell culture using only ethanol and/or methanol as an extraction solvent, to produce the *Camellia sinensis* dedifferentiated stem cell extract.

2. The process according to claim 1, wherein the cell culture is produced by culturing *Camellia sinensis* plant callus cells.

3. The process according to claim 1, wherein the cell culture medium comprises the Hormones 2,4-Dichlorophenoxyacetic acid (2,4-D), Naphthaleneacetic acid (NAA) and 6-Benzylamino purine (BAR).

4. The process according to claim 1, wherein the cell culture medium has a pH of from 5.6 to 6.0.

5. A composition comprising a therapeutically effective amount of the *Camellia sinensis* dedifferentiated stem cell extract obtainable by the process according to claim 1.

6. The composition according to claim 5, wherein the composition is an oral or topical skin treatment composition.

7. The composition according to claim 5, wherein the composition comprises at least 0.01 wt % of the *Camellia sinensis* dedifferentiated stem cell extract.

8. The composition according to claim 7, wherein the composition comprises at least 0.1 wt % of the *Camellia sinensis* stem dedifferentiated cell extract.

* * * * *

UNITED STATES PATENT AND TRADEMARK OFFICE
CERTIFICATE OF CORRECTION

PATENT NO.         : 10,765,622 B2
APPLICATION NO.    : 16/092869
DATED              : September 8, 2020
INVENTOR(S)        : Mark John Berry and Ravine Anthony Gungabissoon Page 1 of 1

It is certified that error appears in the above-identified patent and that said Letters Patent is hereby corrected as shown below:

In the Claims

Column 10, Line 30 should read:
3. The process according to claim 1, wherein the cell culture medium comprises the Hormones 2,4-Dichlorophenoxyacetic acid (2,4-D), Naphthaleneacetic acid (NAA) and 6-Benzylamino purine (BAP).

Signed and Sealed this
Third Day of November, 2020

Andrei Iancu
*Director of the United States Patent and Trademark Office*